US012740838B2

(12) United States Patent
Bar et al.

(10) Patent No.: US 12,740,838 B2
(45) Date of Patent: Sep. 22, 2026

(54) SINGLE ORIGIN MARKER ASSEMBLIES AND METHODS FOR THEIR USE

(71) Applicant: LEM Surgical AG, Bern (CH)

(72) Inventors: Yossi Bar, Muri bei Bern (CH); Lior Kimron, Muri bei Bern (CH); Matvey Rzhavskiy, Muri bei Bern (CH)

(73) Assignee: LEM Surgical AG, Bern (CH)

( * ) Notice: Subject to any disclaimer, the term of this patent is extended or adjusted under 35 U.S.C. 154(b) by 0 days.

(21) Appl. No.: 19/277,719

(22) Filed: Jul. 23, 2025

(65) Prior Publication Data

US 2025/0345134 A1 Nov. 13, 2025

Related U.S. Application Data

(63) Continuation of application No. PCT/EP2024/052373, filed on Jan. 31, 2024.

(60) Provisional application No. 63/442,451, filed on Jan. 31, 2023.

(51) Int. Cl.

*A61B 34/00* (2016.01)
*A61B 34/30* (2016.01)
*A61B 34/20* (2016.01)
*A61B 90/00* (2016.01)

(52) U.S. Cl.

CPC ...... *A61B 34/30* (2016.02); *A61B 2034/2068* (2016.02); *A61B 2090/3916* (2016.02); *A61B 2090/3966* (2016.02); *A61B 2090/3983* (2016.02)

(58) Field of Classification Search

CPC ............................................ A61B 2034/2068

See application file for complete search history.

(56) References Cited

U.S. PATENT DOCUMENTS

| | | | | |
|---|---|---|---|---|
| 12,029,511 | B2 | 7/2024 | Bar | |
| 12,114,946 | B2 | 10/2024 | Bar et al. | |
| 12,508,090 | B2 | 12/2025 | Bar | |
| 2016/0278875 | A1* | 9/2016 | Crawford | A61B 90/98 |
| 2018/0311011 | A1 | 11/2018 | Van Beek et al. | |
| 2019/0274775 | A1 | 9/2019 | Olive et al. | |
| 2024/0164854 | A1 | 5/2024 | Bar | |

(Continued)

FOREIGN PATENT DOCUMENTS

| | | | |
|---|---|---|---|
| EP | 3241518 | A2 | 11/2017 |
| WO | WO-2022195460 | A1 | 9/2022 |

(Continued)

OTHER PUBLICATIONS

PCT/EP2024/052373 International Search Report and Written Opinion dated Mar. 27, 2024.

*Primary Examiner* — Joseph M Santos Rodriguez
(74) *Attorney, Agent, or Firm* — Wilson Sonsini Goodrich & Rosati

(57) ABSTRACT

An integrated marker system used for registration of a pre-operative images with a surgical robot and subsequent robotic navigation during a robotic surgical procedure in includes a registration marker removably pre-attached to a (Continued)

navigation marker in a predetermined relative orientation. The integrated marker system may be placed on a patient's bony anatomy and used in an initial registration step. After completing registration, the registration marker may be removed leaving navigation marker available for robotic navigation and patient tracking.

12 Claims, 4 Drawing Sheets

(56) References Cited

U.S. PATENT DOCUMENTS

| | | | |
|---|---|---|---|
| 2024/0261046 | A1 | 8/2024 | Bar |
| 2024/0268919 | A1 | 8/2024 | Bar |
| 2024/0341877 | A1 | 10/2024 | Bar |
| 2024/0358460 | A1 | 10/2024 | Bar |
| 2024/0366320 | A1 | 11/2024 | Bar |
| 2024/0423728 | A1 | 12/2024 | Bar |
| 2024/0423730 | A1 | 12/2024 | Bar |
| 2024/0423731 | A1 | 12/2024 | Bar |
| 2025/0032208 | A1 | 1/2025 | Bar |
| 2025/0049520 | A1 | 2/2025 | Bar et al. |
| 2025/0114158 | A1 | 4/2025 | Bar |
| 2025/0143813 | A1 | 5/2025 | Bar |
| 2025/0235206 | A1 | 7/2025 | Bar |
| 2025/0345127 | A1 | 11/2025 | Bar et al. |
| 2025/0352289 | A1 | 11/2025 | Bar |

FOREIGN PATENT DOCUMENTS

| | | | |
|---|---|---|---|
| WO | WO-2023067415 | A1 | 4/2023 |
| WO | WO-2023118984 | A1 | 6/2023 |
| WO | WO-2023118985 | A1 | 6/2023 |
| WO | WO-2023144602 | A1 | 8/2023 |
| WO | WO-2023152561 | A1 | 8/2023 |
| WO | WO-2023223215 | A1 | 11/2023 |
| WO | WO-2023237922 | A1 | 12/2023 |
| WO | WO-2023248005 | A1 | 12/2023 |
| WO | WO-2024089473 | A1 | 5/2024 |
| WO | WO-2024160875 | A1 | 8/2024 |
| WO | WO-2024160896 | A1 | 8/2024 |
| WO | WO-2024165397 | A1 | 8/2024 |
| WO | WO-2025008416 | A1 | 1/2025 |
| WO | WO-2025036864 | A1 | 2/2025 |
| WO | WO-2025108905 | A1 | 5/2025 |
| WO | WO-2025119761 | A1 | 6/2025 |
| WO | WO-2025125379 | A1 | 6/2025 |
| WO | WO-2025195791 | A1 | 9/2025 |
| WO | WO-2025195902 | A1 | 9/2025 |
| WO | WO-2025209993 | | 10/2025 |
| WO | WO-2025257316 | A1 | 12/2025 |

* cited by examiner

SINGLE ORIGIN MARKER ASSEMBLIES AND METHODS FOR THEIR USE

CROSS-REFERENCE

This application is a continuation of PCT/EP2024/052373, filed Jan. 31, 2024, which claims the benefit of U.S. Provisional Application No. 63/442,451, filed Jan. 31, 2023, the entirety of which is incorporated herein by reference.

BACKGROUND

Field

The disclosed technology relates generally to medical apparatus, systems, and methods. More particularly, the disclosed technology relates to surgical robots and systems and to methods for image registration and anatomy tracking using such surgical robots.

Surgical robots often rely on real-time optical or other sensor-based tracking of the positions and movement of both patient anatomy and surgical tools within a surgical field. Such tracking is typically performed by scanning the surgical robotic field with one or more optical cameras, but other sensors such as ultrasound, infrared, magnetic, laser (LIDAR), image recognition, and the like, can also be used. Surgical robots typically operate in a three-dimensional robotic coordinate system corresponding to the surgical field and is registered with a pre-operative image of the patient anatomy, e.g., a three-dimensional computer tomographic (CT) image, fluoroscopic image, or the like.

Registration of the pre-operative image with the robotic coordinate system is commonly accomplished using radiopaque "registration" markers or fiducials that are affixed to a patient anatomy, e.g., a bony anatomy in orthopedic and other procedures. The registration markers are usually large, e.g., typically having a minimum dimension of 7 cm, 10 cm, or more, in order to provide accurate imaging and registration. The large size of the registration markers, however, makes them less desirable for use as "navigation" markers during the subsequent robotic surgical procedure. An overly large navigation markers can block the surgeon's access to the surgical field as well as limiting the surgeon's vision. Thus, it is common to replace the large registration markers with smaller navigation markers, typically having a maximum dimension of 5 cm or less, used for tracking the patient anatomy and positioning the robotic arms during a surgical procedure.

For example, a clamp, screw or other fixation member may be placed on the spinal or other bony anatomy of a patient to define an "origin" in a robotic coordinate system. A relatively large registration marker is then coupled to the attachment point for initial registration of a surgical robotic system with a pre-operative image taken by computer tomography (CT), fluoroscopy, or the like. The registration marker may then be removed and replaced with a relatively small navigation marker which is attached to the same attachment point so that it is co-located with the registration marker at the origin.

The smaller registration marker improves the surgeon's access and visibility and, because the marker is typically lighter and has a smaller footprint, is less likely to deform or deflect during of the procedure. For example, in spinal surgery, the patient's spine may flex, torque, or otherwise move during a surgical procedure due to multiple factors. Navigation markers enable a surgical robot to track such movements, but to do so the navigation marker is typically exchanged for the registration marker so that it is located at the same position in the robot coordinate system.

While workable and an improvement over the use of large markers for both registration and navigation, the need to exchange a large registration marker for a smaller navigation marker has disadvantages. For example, the exchange step takes time, extends the duration of the procedure, and increases the chance of human error. Additionally, the exchange step can displace the fixation member, and the need to making two separate attachments can cause misalignments. Even small displacements and misalignments can significantly reduce the accuracy of subsequent tracking based on the navigation marker.

For these reasons, it would be desirable to provide improved surgical markers and fiducials which can be used for both radiographic registration and subsequent optical or other sensor-based navigation. Such improved surgical markers would require only a single implantation step, would remain stable during both registration and navigation with little or no displacement or loss of accuracy, and would minimize any interference with surgeon access and viewing during robotic or other surgical procedures. In addition to such improved markers, it would be desirable to provide surgical robotic systems and methods configured to use such markers. While particularly suitable for use with surgical robots and in surgical robotics procedures, the improved surgical markers and fiducials of the disclosed technology can be used in any system or method which combines both initial radiographic registration and subsequent optical or other sensor-based navigation. At least some of the objectives will be met by the description and claimed herein.

SUMMARY

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The apparatus, systems, and methods of the disclosed technology provide accurate registration by using a large registration marker component and provide improved navigation by using a smaller navigation marker that reduces interference with the surgeon's vision of and access to the surgical field. The initial accuracy is largely retained as the navigation marker is co-located with the registration marker, allowing the registration marker to be removed while maintaining the navigation marker precisely at the initial attachment location. The physical displacement between the registration marker and the navigation can be marker components of the integrated surgical marker can be offset or "canceled out" based on the known dimensions of the integrated surgical marker or by scanning the integrated surgical marker after implantation.

In a first aspect, the disclosed technology provides a robotic surgical system for use with an integrated surgical marker comprising a registration marker removably pre-attached to a navigation marker in a predetermined relative orientation. The robotic surgical system comprises a surgical robot including at least one robotic arm and a controller. The controller is configured to (a) register an image of a patient's bony anatomy to a robotic coordinate system based upon a location of the registration marker in the image while the registration marker remains attached to the navigation marker and (b) control motion of the at least one robotic arm based upon a tracked location of the navigation marker after the registration marker has been removed from the navigation marker.

While the disclosed technology is particularly suitable for scanning and tracking the navigation marker after the registration marker has been removed, in some instances the control system can scan, track, and/or utilize the navigation marker for robotic system control prior to detachment of the registration marker. While detachment of the registration marker will often occur early in a robotic surgical procedure, the disclosed technology includes detachment of the registration marker at any point during a robotic surgical procedure.

Using such a robotic surgical system, an initial registration can be performed using a relatively large registration marker to provide high accuracy. The registration marker can then be removed, leaving the smaller navigation marker in place minimizing interference with a surgeon's access to and vision while the robotic procedure is performed. Removing the registration marker from the implanted navigation marker significantly reduces the risk of displacing the navigation marker and the time need to perform the surgical procedure in comparison to prior art techniques which rely on exchanging a navigation marker for a registration marker.

In some embodiments, the surgical system further comprises a surveillance arm carrying a surveillance sensor, wherein the controller is further configured to scan or otherwise image the registration marker with the surveillance sensor to register the image of the patient's bony anatomy with a robotic coordinate system.

In some embodiments, the surgical system further comprises a navigation sensor carried by a robotic arm wherein the controller is further configured to track the navigation marker with the navigation sensor to track the patient anatomy during a robotic surgical procedure after the registration marker has been removed.

In some embodiments, the controller is further configured to calculate initial positional coordinates of the navigation marker within the robotic coordinate system by translating initial positional coordinates of the registration marker within the robotic coordinate system based upon a known or measured physical offset between the registration marker and the navigation marker prior to removal of the registration marker to allow the navigation sensor to track movement of the bony anatomy based upon tracking the location of the navigation marker during a surgical procedure.

In some embodiments, the controller is configured to calculate the initial positional coordinates of the navigation marker by translating the initial positional coordinates of the registration marker based upon the dimensions of the integrated surgical marker when fully assembled.

In some embodiments, the controller is configured to calculate the initial positional coordinates of the navigation marker relative to the initial positional coordinates of the registration marker by scanning the registration marker and the navigation marker and calculating the physical offset of registration marker and the navigation markers the robot coordinate system.

In some embodiments, the surgical robot comprises at least two working robotic arms configured to hold and manipulate surgical tools.

In some embodiments, the surgical robot is mounted on a rigid support structure which defines the robotic coordinate system.

In a second aspect, the disclosed technology provides a method for performing a surgical procedure on a patient using a surgical robot having at least two robotic arms controlled by a controller. The method comprises implanting an integrated surgical marker at an implantation location on a patient's bony anatomy, where (a) the integrated surgical marker includes a registration marker removably attached to a navigation marker in a predetermined orientation relative to the registration marker and (b) the registration marker and the navigation marker have a fixed positional offset when attached. The patient is scanned or otherwise imaged to produce a registration image showing the location of the registration marker in the bony anatomy. A location of the registration marker is registered in a robotic coordinate system of the surgical robot to the location of the registration marker in the image, and the controller calculates a location of the navigation marker in the robotic coordinate system based on a positional offset between the registration marker and the navigation marker in the robotic coordinate system. The registration marker is removed from the integrated surgical marker leaving the navigation marker in place, and the patient is tracked by optically or otherwise observing changes in the location of the navigation marker in the robotic coordinate system during the robotic surgical procedure.

In some embodiments, scanning the patient to produce the registration image comprises at least one of fluoroscopic imaging and computed tomography (CT).

In some embodiments, the registration image comprises a digital file which is provided to the controller of the surgical robot.

In some embodiments, the controller calculates initial coordinate points for the navigation marker in the robotic coordinate system using a translational transfer function to reposition initial coordinate points of the registration marker based upon the positional offset between the registration marker and the navigation marker.

In some embodiments, registering the location of the registration image in the robotic coordinate system comprises the controller sensing a location of the registration marker while the patient is present within a surgical space defined by the robotic coordinate system.

In some embodiments, sensing the location of the registration marker comprises the controller scanning the registration marker patient with a camera.

In some embodiments, scanning the registration marker comprises the controller manipulating an arm of the robot to position the camera to view the registration marker.

In some embodiments, scanning changes in the location of the navigation marker comprises the controller manipulating an arm of the robot to position said camera to view the registration marker.

In some embodiments, the controller (a) manipulates a surveillance arm to position a surveillance camera to scan the patient to produce a registration image and (b) manipulates a navigation arm to track changes in the location of the navigation marker in the robotic coordinate system during the robotic surgical procedure.

In some embodiments, the positional offset is known based upon the geometry of the integrated surgical marker prior to removal of the navigation marker.

In some embodiments, the methods of the disclosed technology further comprise the controller calculating the positional offset by scanning the integrated surgical marker prior to removal of the navigation marker.

In a third aspect, the disclosed technology provides an integrated surgical marker comprising a navigation marker and a registration marker. The navigation marker has an attachment feature configured to be temporarily attached to a patient's bony anatomy, and the registration marker is removably pre-attached to the navigation marker in a predetermined orientation relative to the navigation marker.

In some embodiments, the attachment features comprise a post configured to be directly or indirectly implanted in bone.

In some embodiments, the attachment features comprise a coupling element configured to receive or attach to a member implanted in bone.

In some embodiments, the registration marker comprises a planar array of radiopaque features.

In some embodiments, the navigation marker comprises an optically visible planar target.

In some embodiments, the navigation marker further comprises an array of radiopaque features on the planar target.

In some embodiments, the planar array and the planar target are attached at an angle in a range from 20° to 90°, usually from 30° to 60°.

In some embodiments, the attachment features is configured to hold the registration marker generally flat over the patient's anatomy with the navigation marker extending upwardly from the patient anatomy.

In some embodiments, the planar array of the registration marker has a minimum dimension of 7 cm and the planar target of the navigation marker has a maximum dimension of 5 cm.

Accordingly, provided herein are systems and methods for registration and navigation using an "integrated" marker in a robotic surgical system with navigation capabilities. Such "integrated" surgical markers combine both a registration marker and a navigation marker in a single, rigid assembly which can implanted at a target attachment site in a patient's anatomy, typically a bone or other hard tissue anatomy, such as a spinal vertebra. Implantation may be accomplished using an attachment feature, typically a clamp, post or the like which can be implanted. Usually, the attachment feature will be permanently affixed to the navigation marker but in some embodiments may be a separate component, e.g., a free post which can be implanted with the navigation marker attached after the implantation of the post.

Such integrated marker will typically be used with a multi-arm surgical robotic system comprising at least two, three, or more robotic arms. At least one arm will be configured to perform surgical tasks and at least one arm will be configured to carry and operate at least one camera or other sensor as part of a robotic navigation system.

The robotic arms are typically mounted to operate in a single robotic coordinate system, often being mounted on a single mobile or other chassis and being controlled by a controller that is mounted on the same single chassis. In some embodiments, the "working" surgical arms which carry surgical tools may be mounted on a single chassis and the "surveillance" or "navigation" arm(s) which carry cameras or other sensors may be on separate cart(s) or chassis(es). A variety of specific robotic surgical systems that may be used with the integrated markers of the disclosed technology are described in the commonly owned US and PCT patent publications listed and incorporated-by-reference above.

The navigation marker of integrated surgical markers may be implanted on the bony anatomy of a patient in any conventional manner so long as the attachment is stable and resists displacement during the surgical procedure. Exemplary attachment means include using a clamp, a Schanz screw, or any other bony fixation or attachment feature. In representative embodiments, the integrated marker system is assembled prior to implantation with the registration marker being rigidly (but detachably) connected to the navigation marker in a predetermined relation, and with the integrated unit then being placed on the bony attachment unit in that configuration.

In some embodiments, the registration marker is sufficiently large to provide accurate registration with the bony anatomy of a patient in a surgical robotic system. After a registration step, the registration marker component may be detached from the navigation marker component and removed from the surgical field, e.g., by removing an attachment screw or other fastener. Such detachment may be accomplished with minimum or no displacement of the navigation marker, assuring little or no loss of accuracy during subsequent navigation and tracking by the robotic surgical system which relies on accurate placement of the navigation marker.

In further embodiments, a method for registration and navigation in a surgical procedure using a surgical robotic system with navigation capabilities is provided. An integrated marker s comprising a registration component and a navigation component is provided and is attached to the bony anatomy of a patient by conventional means. A registration step is then carried out with a modality such as CT or x-ray, after which the registration component of the integrated marker system is removed, leaving behind a navigation marker that can be used to accurately track the patient anatomy during the subsequent steps of a robotic surgical procedure such as a spinal robotic surgical procedure.

INCORPORATION BY REFERENCE

Relevant commonly owned publications and applications include PCT/IB2022/052297 (published as WO2022/195460); PCT/2022/058988 (published as WO2023/067415); PCT/IB2022/058972 (published as WO2023/118984); PCT/IB2022/058982 (published as WO2023/118985); PCT/IB2022/058978 (published as WO2023/144602); PCT/IB2022/058980 (published as WO2023/152561); PCT/IB2023/055047 (published as WO2023/223215); PCT/IB2022/058988 (published as WO2023/237922); PCT/IB2023/055439; PCT/IB2023/056911; PCT/IB2023/055662; PCT/IB2023/055663; U.S. 63/524,911; and U.S. 63/532,753, the full disclosures of which are incorporated herein by reference.

The full disclosures of PCT Application PCT/EP2024/052338, Mathys Reference: P77439WO entitled "METHODS AND SYSTEMS FOR TRACKING MULTIPLE OPTICAL MARKERS IN A ROBOTIC SURGICAL PROCEDURE," and PCT Application PCT/EP2024/052353, Mathys Reference: P77440WO entitled "INTEGRATED MULTI-ARM MOBILE MODULAR SURGICAL ROBOTIC SYSTEM," both of which are filed on the same day as the present application, are incorporated herein by reference in their entirety.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosed technology are set forth with particularity in the appended claims. A better understanding of the features and advantages of the disclosed technology will be obtained by reference to the following detailed description that sets forth illustrative embodiments, in which the principles of the disclosed technology are utilized, and the accompanying drawings of which:

DETAILED DESCRIPTION

Figure 1:
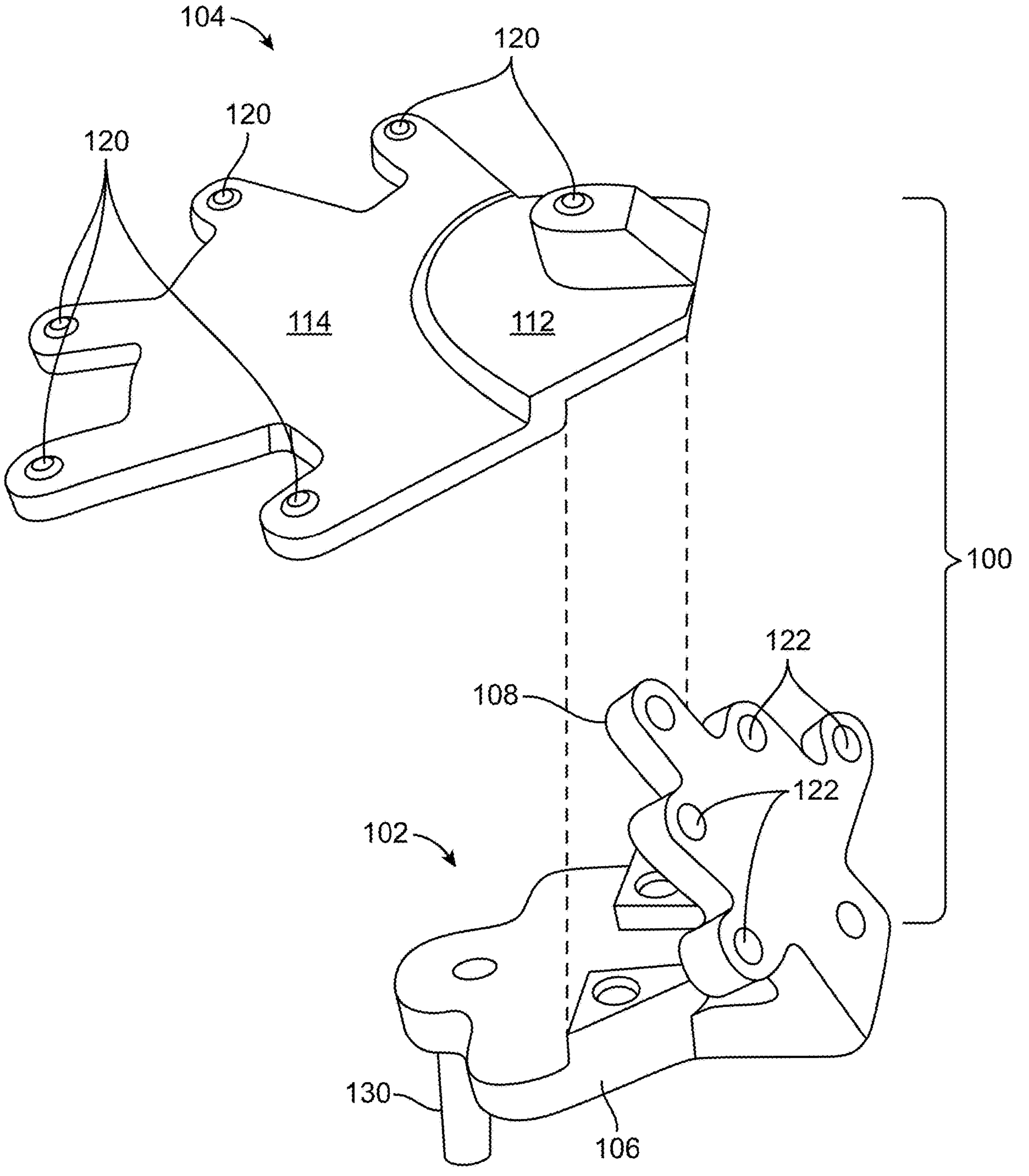
FIG. 1 is an isometric view an integrated surgical marker constructed in accordance with the principles of the disclosed technology having a registration marker (above) detached from a navigation marker (below), in accordance with some embodiments.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The constraints of using cameras and other sensors to track registration and navigation markers in robotic surgical procedures are well known. For example, the accuracy of optically scanning and tracking a marker or fiducial is inversely related to the distance between the camera/sensor and the marker and directly related to the size of the markers. Thus, larger markers and closer cameras will generally improve the accuracy of tracking. Unfortunately, large markers and close camera positioning can often interfere with a surgeon's ability to efficiently perform a surgery. Such limitations are particularly acute during initial registration of the robotic coordinate system with the patient's pre-operative scan where the camera may be remote, and accuracy is critical as any errors will be carried through an entire surgical procedure.

The disclosed technology maximizes the accuracy of the initial registration step while minimizing marker interference during subsequent performance of the surgical procedure. The systems, apparatus, and methods of the disclosed technology allow registration to be performed using large registration markers, e.g., having a planar or other array of radiopaque (RO) or other features with minimum dimension of at least 7 cm, usually at least 10 cm, to provide a desired accuracy, e.g., ±1 mm to 2 mm at tool tip when the camera is placed at a standard distance from the patient, e.g., from 1.5 meters to 2.5 meters from the navigation marker. The disclosed technology, however, allows the large registration markers to be removed before the surgical procedure is commences, leaving smaller navigation markers in place with a reduced risk of interference. For example, in cases where the larger registration marker might be located over a surgical opening, the smaller navigation marker can be located to avoid the surgical opening.

In contrast to the registration markers, the navigation markers of the disclosed technology will usually be smaller, typically having a planar or other target with a maximum dimension of 5 cm, often a maximum dimension of 3 cm.

The apparatus, systems and methods of the disclosed technology are described with specific reference to the attached figures. One of skill in the art will realize that the described embodiments are representative in nature and reasonable departures from the described embodiments are still possible while staying within the scope of the disclosed technology.

Figure 2:
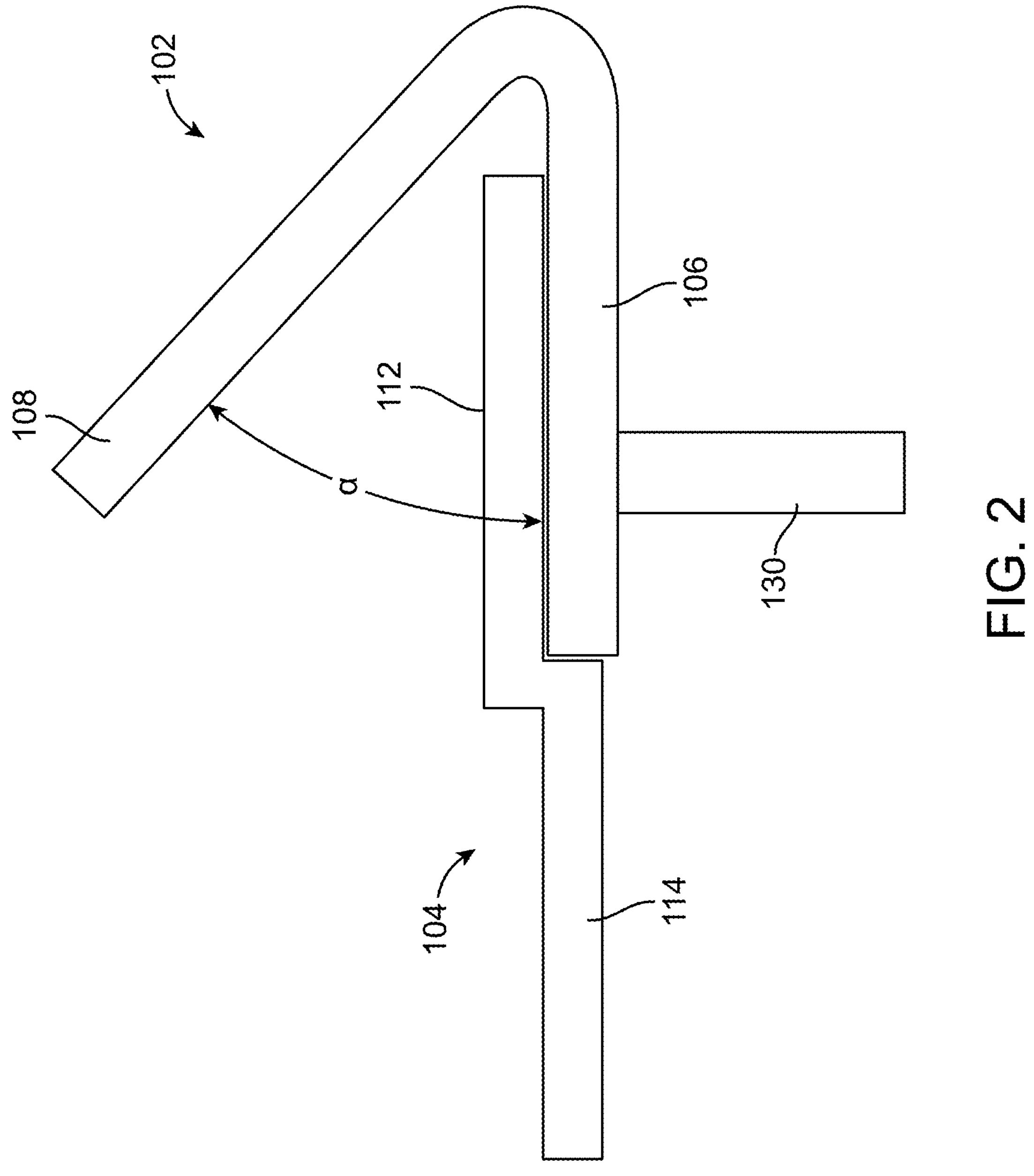
FIG. 2 is a simplified side view of the integrated surgical marker of FIG. 1 showing a geometric relationship of the registration marker and the navigation marker, in accordance with some embodiments.
Figure 3:
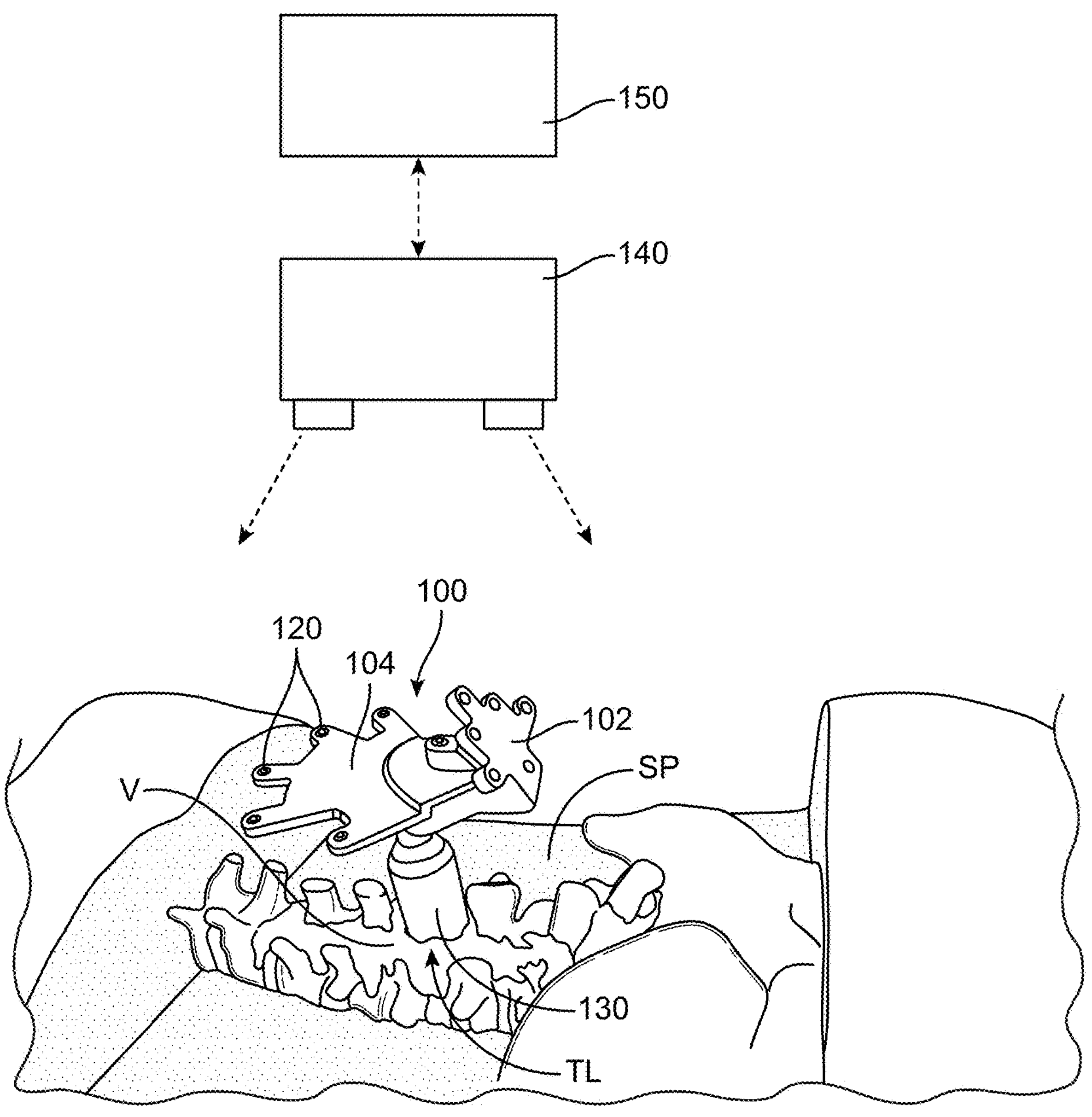
FIG. 3 shows the integrated surgical marker of FIG. 1 in a fully assembled configuration with the navigation marker attached to a bony anatomy of a patient according to the principles of the disclosed technology, in accordance with some embodiments.

FIGS. 1 and 2 show an integrated surgical marker 100 constructed in accordance with the principles of the disclosed technology, in accordance with some embodiments. The integrated surgical marker 100 may comprises a registration marker 102 and a navigation marker 106 that can be assembled into an integrated unit, as shown in FIG. 3. A flange 112 of the registration marker 104 can be detachably secured to a base 106 of the navigation marker 102 using screws, clips, clamps or other conventional fasteners (not shown). The attachment may be rigid when the markers 102 and 104 are assembled and allow the surgeon or other user to easily detach the registration marker while the navigation marker 102 remains implanted in a bony or other target location in the patient.

The registration marker 104 may comprise a flat or planar target 114 having a planar array of RO beads 120 (for example, tungsten or stainless-steel beads) distributed over an upper surface thereof, typically having at least three beads, more typically at least five beads, or more. An initial registration scan may be performed using CT, fluoroscopy, or other or X-ray imaging techniques, and the pattern of RO or other scannable beads 120 may be selected to allow both the location and orientation of the registration marker 104 to be identified in the registration image. Alternatively or additionally, the registration marker 104 can contain elements that are visible in MRI (e.g., gadolinium), ultrasound, or other scanning modality, and an initial registration step can be performed using the alternate scanning technology.

While flat or planar markers surface are convenient and can simplify scanning and tracking protocols, it will be appreciated that non-planar surfaces could be used in some embodiments so long as the surface configuration is accounted for in scanning and tracking calculations.

The navigation marker 102 may include a planar target 108 attached to the base 106 at an angle α, typically in a range from 20° to 90°, usually from 30° to 60°. Such orientation may be advantageous as it allows the registration marker 104 to lie closer to the patent during the registration scan and elevate the planar target 108 of the smaller navigation marker 102 for better tracking during subsequent performance of the robotic surgical procedure. While the navigation marker 102 is usually intended for optical tracking by a camera of the robotic system, it may optionally include RO markers 122 to allow scanning in the initial registration scan or during the robotic procedure, for example using a fluoroscope present at the surgical table.

The navigation marker 102 also may include an attachment feature 130, such as a post, screw, or the like, that can be directly implanted in the patient's bony anatomy. Alternatively, the attachment feature could be configured to couple to a separate post, screw or other anchor that has been previously implanted in the bony anatomy. In some cases, the attachment feature could be a bore or other cavity in the base that is configured to couple with a separately implanted anchor.

The navigation marker 102 can be used primarily with optical tracking, e.g., using a camera. In some embodiments, other navigation markers could be configured for use with navigation systems that rely on ultrasound tracking, infrared tracking, image recognition, laser tracking such as LIDAR, magnetic tracking, and the like. Moreover, while the integrated surgical markers of the disclosed technology will be used primarily in surgical robotic systems, in some embodiments they could be used with any conventional surgical navigation system that is not integrated into or otherwise used with a surgical robot.

Exemplary methods according to the disclosed technology may comprise attaching the integrated surgical marker 100 to a patient anatomy, such as a vertebra V in the patient's spine SP, as shown in FIG. 3. The spine is surgically exposed and the integrated surgical marker 100 and the attachment feature 130 rigidly attached to a target location TL in the spine, e.g., any one of L1 to L5 in the lumbar spine. The disclosed technology, however, is not limited to any particular patient anatomy and any target anatomy can allow for rigid or near rigid attachment of the integrated surgical marker 100 so that said attachment remains stable over the entire course of a surgical procedure.

Attachment may be effected in any conventional manner, for example using a clamp, a bone screw, e.g., a Schanz screw, or any other bony fixation or attachment feature in the case of spinal attachment. Other attachment means may be more appropriate in non-spinal anatomy, and for the disclosed technology, the attachment may remain stable during both registration and navigation phases of the robotic or other surgical procedure.

After the integrated surgical marker 100 has been stably attached to the bony or other patient anatomy, a CT or other suitable scan may be performed to register the bony anatomy of the patient with the coordinate system of the surgical robot ("robotic coordinate system"). An image file showing the location of the integrated surgical marker 100, including at least the registration marker 104, in the image of the anatomy may be provided to a controller 150 of the surgical robot, and the controller may register the patient anatomy to the robotic coordinate system in a conventional manner, typically by optically scanning the patient anatomy including at least the registration marker 104, with a registration camera 140, as shown in FIG. 3. While the navigation marker 102 may also be included in the initial registration scan, and in some cases could also be used in the initial registration calculation by the controller 150, the navigation marker is not necessary to accomplish registration in accordance with the principles of the disclosed technology. Interference of the navigation marker 102 with the registration scan of the registration marker may be avoided.

Figure 4:
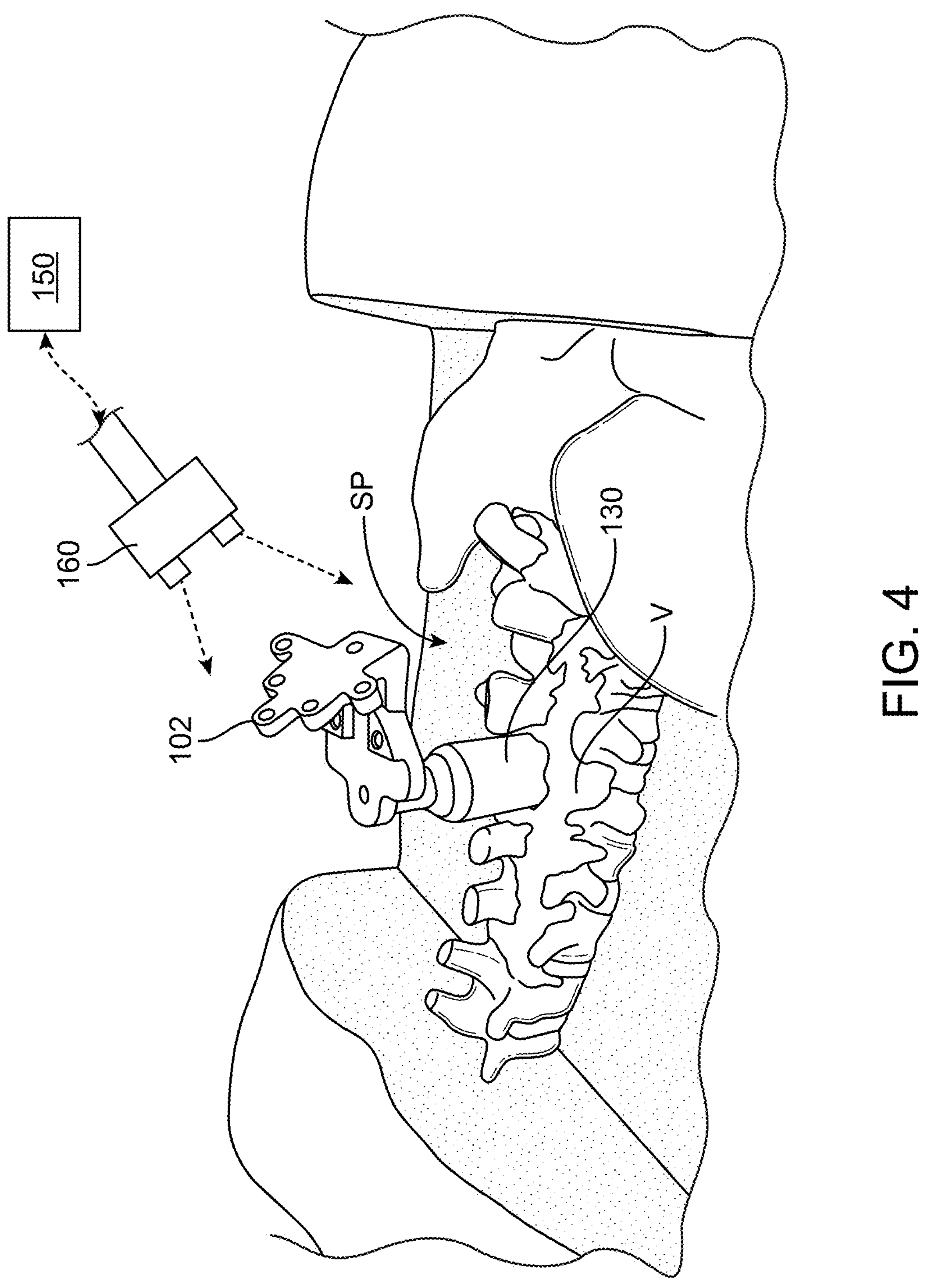
FIG. 4 shows the integrated surgical marker of FIG. 1 after the registration marker has been detached from the navigation marker which remains attached to the bony anatomy of the patient according to the principles of the disclosed technology, in accordance with some embodiments.

After the registration step has been completed, the registration marker 104 may be detached from the navigation marker 102 and removed from the surgical field, as shown in FIG. 4. The navigation marker 102 may remain in place and can be tracked with a navigation camera 150 of the surgical robot. The position of the navigation marker 102 is displaced from that of the registration marker 104 in the initial scan, so the surgical robot may compensate for such displacement when scanning, tracking, and controlling during a surgical procedure.

To compensate for such displacement, the controller 150 may calculate the displacement of the navigation marker 102 relative to the registration marker 104 in the image scan in either of at least two ways. Usually, the controller 150 may use a "translational transfer function" based upon the known physical displacement between the registration and navigation markers in the fully assembled integrated surgical marker 100. For example, if the location of the registration marker 104 in the robotic coordinate system is $X_1$, $Y_1$, $Z_1$, the location of the navigation marker 102 ($X_2$, $Y_2$, $Z_2$) can be calculated as follows:

$$X_2,\ Y_2,\ \text{and}\ Z_2 = X_1 + D_X,\ Y_1,\ +D_Y,\ \text{and}\ Z_1 + Dz$$

where $D_X$, $D_Y$, and $D_Z$ represent displacements of the of navigation marker 102 relative to the registration marker 104 in the X-, Y-, and Z-directions in a Cartesian coordinate system. Other equations can be used in polar and other coordinate systems.

Alternatively, the displacement between the registration marker 104 and the navigation marker 102 can be determined by scanning the fully assembled integrated surgical marker 100, e.g., using the registration camera 150, where the controller 150 can determine X-, Y-, and Z-displacements based upon the scan. Determining displacements based upon a scan, however, may generally be less accurate and less desirable.

As shown in FIG. 4, after registration has been completed, the registration marker 104 (FIG. 3) may be detached from the navigation marker 102 and removed from the surgical space. The navigation marker 102 may remain rigidly affixed to the attachment feature 130 (with a significantly reduced footprint) and can be scanned and tracked by the controller 150 of the surgical robot, for example using a navigation camera 160, as described in commonly owned PCT Application PCT/EP2024/052338, Mathys Reference P77439WO), entitled "METHODS AND SYSTEMS FOR TRACKING MULTIPLE OPTICAL MARKERS IN A ROBOTIC SURGICAL PROCEDURE," and filed on the same day as the present application, the full disclosure of which is incorporated herein by reference.

REFERENCE NUMBERS

100 integrated surgical marker
102 navigation marker
104 registration marker
106 planar base
108 planar target
112 attachment flange
114 planar target
120 registration RO beads
122 RO beads navigation
130 attachment feature
140 registration camera
150 robotic controller
160 navigation camera All embodiments described and claimed herein may be used in conjunction with a variety surgical robotic system. The surgical robotic system may take many forms as it may be a single arm system or a multi arm system. A multi-arm surgical robotic system used in conjunction with the present system and methods may take the form of multiple robotic arms mounted on a single mobile chassis, or multiple robotic arms in a bed or floor mounted format, or multiple robotic arms each mounted to its own mobile chassis. A multi-arm surgical robotic system used in conjunction with the present systems and methods may also have integrated robotic navigation capabilities or may make use of a separate navigation system. One of skill in the art will understand that a surgical robotic system is optional for use of the disclosed system and methods. All that is required for the present disclosure is a surgical context where sequential use of registration and navigation are desirable and where there would be a benefit to enhanced accuracy and improved surgeon workflow and line of sight to the surgical field.

One of skill in the art will also understand that variations on the described embodiments are possible, such as the placement of additional navigation markers on adjacent anatomy or on a CT device. Also, while representative embodiments are shown in spinal surgery, the integrated marker system of the disclosed technology can also be used in other surgical fields.

While some embodiments of the disclosed technology have been shown and described herein, it will be obvious to those skilled in the art that such embodiments are provided by way of example only. Numerous variations, changes, and substitutions will now occur to those skilled in the art without departing from the scope of the invention. It should be understood that various alternatives to the embodiments of the invention described herein may be employed in practicing the invention. It is intended that the following claims define the scope of the technology and that methods and structures within the scope of these claims and their equivalents be covered thereby.

What is claimed is:

1. A method for performing a surgical procedure on a patient using a surgical robot having at least two robotic arms controlled by a controller, the method comprising:

implanting an integrated surgical marker at an implantation location on a patient's bony anatomy, wherein the integrated surgical marker includes a registration marker removably attached to a navigation marker in a predetermined orientation relative to the registration marker, wherein the registration marker and the navigation marker have a fixed positional offset when attached;

scanning the patient to produce a registration image showing a location of the registration marker in the bony anatomy;

registering a location of the registration marker in a robotic coordinate system of the surgical robot to the location of the registration marker in the image;

wherein the controller calculates a location of the navigation marker in the robotic coordinate system based on a positional offset between the registration marker and the navigation marker in the robotic coordinate system;

removing the registration marker from the integrated surgical marker and leaving the navigation marker in place; and tracking changes in the location of the navigation marker in the robotic coordinate system during the robotic surgical procedure.

2. The method of claim 1, further comprising tracking changes in the location of the navigation marker in the robotic coordinate system before the registration marker has been removed.

3. The method of claim 1, wherein scanning the patient to produce the registration image comprises at least one of fluoroscopic imaging or computed tomography (CT).

4. The method of claim 3, wherein the registration image comprises a digital file which is provided to the controller of the surgical robot.

5. The method of claim 1, wherein the controller calculates initial coordinate points for the navigation marker in the robotic coordinate system using a translational transfer function to reposition initial coordinate points of the registration marker based upon the positional offset between the registration marker and the navigation marker.

6. The method of claim 1, wherein registering the location of the registration image in the robotic coordinate system comprises the controller sensing a location of the registration marker while the patient is present within a surgical space defined by the robotic coordinate system.

7. The method of claim 6, wherein sensing the location of the registration marker comprises the controller tracking the registration marker patient with a camera.

8. The method of claim 7, wherein tracking the registration marker comprises the controller manipulating an arm of the at least two robotic arms to position the camera to view the registration marker.

9. The method of claim 8, wherein tracking the registration marker comprises the controller manipulating an arm of the at least two robotic arms to position the camera to view the registration marker.

10. The method of claim 9, wherein the controller (a) manipulates a surveillance arm of the at least two robotic arms to position a surveillance camera to scan the patient to produce the registration image, and (b) manipulates a navigation arm of the at least two robotic arms to track changes in the location of the navigation marker in the robotic coordinate system during the robotic surgical procedure.

11. The method of claim 1, wherein the positional offset is known based upon a geometry of the integrated surgical marker prior to removal of the navigation marker.

12. The method of claim 1, further comprising the controller calculating the positional offset by scanning the integrated surgical marker prior to removal of the navigation marker.

* * * * *